United States Patent
Junius et al.

(10) Patent No.: US 8,605,916 B2
(45) Date of Patent: Dec. 10, 2013

(54) METHOD FOR ADJUSTING A HEARING DEVICE WITH IN-SITU AUDIOMETRY AND HEARING DEVICE

(75) Inventors: Dirk Junius, Möhrendorf (DE);
Johannes Lauer, Baiersdorf (DE);
Matthias Müller-Wehlau, Erlangen (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 140 days.

(21) Appl. No.: 13/245,049

(22) Filed: Sep. 26, 2011

(65) Prior Publication Data
US 2012/0076313 A1    Mar. 29, 2012

(30) Foreign Application Priority Data
Sep. 24, 2010  (DE) .......................... 10 2010 041 337

(51) Int. Cl.
*H04R 29/00*    (2006.01)
(52) U.S. Cl.
USPC .......................................................... 381/60
(58) Field of Classification Search
USPC .......................................................... 381/60
See application file for complete search history.

(56) References Cited

U.S. PATENT DOCUMENTS

| 7,302,069 B2 | 11/2007 | Niederdränk et al. |
| 7,715,577 B2 | 5/2010 | Allen et al. |
| 2012/0140937 A1* | 6/2012 | Poe et al. ................. 381/60 |
| 2012/0302859 A1* | 11/2012 | Keefe ..................... 600/383 |

FOREIGN PATENT DOCUMENTS

| DE | 103 43 291 B3 | 4/2005 |
| WO | 2006/044644 A2 | 4/2006 |

* cited by examiner

*Primary Examiner* — Curtis Kuntz
*Assistant Examiner* — David J Ho
(74) *Attorney, Agent, or Firm* — Laurence A. Greenberg; Werner H. Stemer; Ralph E. Locher

(57) ABSTRACT

The adjustment of a hearing device is to be improved and configured in a more user-friendly fashion. To this end, a method is proposed whereby the hearing device is set individually to the user and is inserted at least partially into the auditory canal of the user. Finally an in-situ measurement of the acoustic impedance of the auditory system of the user including at least part of the auditory canal of the user is implemented with a tympanometric method. An automatic correction of the individual setting of the hearing device can take place on the basis of the results of the in-situ measurement.

9 Claims, 3 Drawing Sheets

METHOD FOR ADJUSTING A HEARING DEVICE WITH IN-SITU AUDIOMETRY AND HEARING DEVICE

CROSS-REFERENCE TO RELATED APPLICATION

This application claims the priority, under 35 U.S.C. §119, of German application DE 10 2010 041 337.2, filed Sep. 24, 2010; the prior application is herewith incorporated by reference in its entirety.

BACKGROUND OF THE INVENTION

Field of the Invention

The present invention relates to a method for adjusting a hearing device to a user by setting the hearing device individually to the user and inserting the hearing device at least partially into the auditory canal of the user. Furthermore, the present invention relates to a hearing device with a signal processing facility, which can be individually set to a user and with a section which can be inserted into an auditory canal of the user.

Hearing devices are wearable hearing apparatuses which are used to supply the hard-of-hearing. To accommodate the numerous individual requirements, different configurations of hearing devices such as behind-the-ear hearing devices (BTE), hearing device with an external receiver (RIC: receiver in the canal) and in-the-ear hearing devices (ITE), e.g. also concha hearing devices or canal hearing devices (ITE—in-the-ear, CIC—completely in the canal) are provided. The hearing devices given by way of example are worn on the outer ear or in the auditory canal. Furthermore, bone conduction hearing aids, implantable or vibrotactile hearing aids are also available on the market. In such cases the damaged hearing is stimulated either mechanically or electrically.

Essential components of the hearing devices include in principal an input converter, an amplifier and an output converter. The input converter is generally a recording transducer, e.g. a microphone and/or an electromagnetic receiver, e.g. an induction coil. The output converter is mostly realized as an electroacoustic converter, e.g. a miniature loudspeaker, or as an electromechanical converter, e.g. a bone conduction receiver. The amplifier is usually integrated into a signal processing unit. This basic structure is shown in the example in FIG. 1 of a behind-the-ear hearing device. One or more microphones 2 for recording the ambient sound are incorporated in a hearing device housing 1 to be worn behind the ear. A signal processing unit 3, which is similarly integrated into the hearing device housing 1, processes the microphone signals and amplifies them. The output signal of the signal processing unit 3 is transmitted to a loudspeaker and/or receiver 4, which outputs an acoustic signal. The sound is optionally transmitted to the ear drum of the device wearer via a sound tube, which is fixed with an otoplastic in the auditory canal. The power supply of the hearing device and in particular of the signal processing unit 3 is supplied by a battery 5 which is likewise integrated into the hearing device housing 1.

Hearing devices are primarily adjusted to the user in consideration of the individual audiogram. In this case modern hearing devices partly provide an opportunity of determining the audiogram solely with the aid of the hearing device itself, and without special devices. With this in-situ audiometry, the test tone is output via the receiver of the hearing device and increased in terms of level until the tone is perceived by the wearer of the hearing device. The resulting level and thus the estimated auditory threshold is either measured here by way of special microphones in the auditory canal or estimated by knowledge of the output level of the receiver in the case of a calibrated hearing device.

The described methods of setting and/or adjusting a hearing device are disadvantageous on the one hand in that, unlike determination of the audiogram with the aid of an audiometer, it is not possible to determine the sound conduction auditory threshold. The sound conduction auditory threshold is a measure of the extent to which the sound conduction (air conduction and bone conduction) is ensured by the outer and middle ear. With the supply with hearing devices, a possible sound conduction hearing impairment is basically treated differently to a purely sensorineural hearing impairment whereby the inner ear is damaged.

The known adjustment methods are nevertheless also disadvantageous in that when determining the auditory threshold, the measurement of the presentation level generally takes place by means of the audiogram in the plane of the hearing device and not in the region of the ear-drum. The frequency-dependent deviation which results therefrom can in some instances distort the measured auditory threshold.

SUMMARY OF THE INVENTION

It is accordingly an object of the invention to provide a method for adjusting a hearing device with in-situ audiometry and a hearing device which overcome the above-mentioned disadvantages of the prior art methods and devices of this general type, which facilitates an adjustment of the hearing device particularly for the hearing device wearer.

In accordance with the invention, the object is achieved by a method for adjusting a hearing device to a user by setting the hearing device individually to the user, and inserting the hearing device at least partially into the auditory canal of the user, as well as in-situ measurements of the acoustic impedance of the hearing system of the user including at least a part of the auditory canal of the user with a tympanometric method and automatically correcting the individual setting of the hearing device with the aid of the result of the in-situ measurement.

Furthermore, provision is made in accordance with the invention for a hearing device with a signal processing facility, which can be individually set to a user, and a section, which can be inserted into an auditory canal of the user, as well as with a measuring facility, with which the acoustic impedance of the hearing system of the user including at least one part of the auditory canal of the user can be measured with a tympanometric method when the section is inserted into the auditory canal. It is possible to automatically correct the individual setting of the signal processing facility with the aid of the tympanometric measurement.

It is thus advantageously possible to achieve a better supply directly at the ear-drum. This is ensured by the sound conduction being taken into consideration by in-situ measurement during the adjustment. As a result, the setting of the hearing device can be adjusted very individually to the auditory canal shape, the fit of the hearing device in the auditory canal and the impedance of the ear.

The individual setting of the hearing device preferably takes place with an audiogram. A good basic setting of the hearing device can therefore be achieved before use of the hearing device.

The hearing device can contain a vent, which is temporarily closed for the in-situ measurement. The method can therefore also be used with an open supply.

It is particularly advantageous if, in the case of the in-situ measurement, a test tone with a constant level is output by the hearing device with a frequency between 200 Hz and 300 Hz. The frequency preferably lies in the range between 220 Hz and 230 Hz. It is therefore sufficiently low in order essentially to obtain a dependency on the rigidity of the auditory components, and sufficiently high so as not to be negatively influenced by low-frequency interference sound.

The ear-drum can be made temporarily hard-walled for the in-situ measurement. A changed impedance is produced as a result, which primarily supplies information relating to the auditory canal upstream of the ear-drum.

It is possible to determine from the in-situ measurement whether the auditory canal is closed to a predetermined degree. It is namely possible to immediately determine from the tympanogram whether the hearing device sits precisely in the auditory canal or whether an, if necessary, existing vent is adequately sealed for the measurement.

It is also advantageous if a difference of two in-situ measurements, one in the case of hard-walled ear-drum and the other in the case of a non-hard-walled ear drum, is used to automatically correct the setting. It is namely possible to deduce the sound portion which penetrates the middle ear from this difference. This provides information about the functionality of the middle ear. The amplification of the hearing device can be corrected in a frequency-dependent fashion accordingly.

The inventive hearing device can be embodied in an embodiment such that the measuring facility includes a microphone, which is integrated into the section of the hearing device which can be inserted into the auditory canal. With an ITE hearing device for instance, a microphone can be arranged on the side of the hearing device which faces the ear-drum. In-situ measurements are thus possible without any problem.

Other features which are considered as characteristic for the invention are set forth in the appended claims.

Although the invention is illustrated and described herein as embodied in a method for adjusting a hearing device with in-situ audiometry and a hearing device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The exemplary embodiments described below represent preferred embodiments of the present invention.

The idea underlying the invention makes provision for measuring the auditory canal volume and the acoustic impedance using tympanometry methods (measuring methods for the mobility of the ear-drum and middle ear) under different conditions within the scope of in-situ audiometry and as a result makes provision for calculating individual corrections for the audiogram and/or being able to automatically perform corrections on the setting of the hearing device.

The acoustic impedance is a measure of the active resistance of an acoustic system. With low frequencies, the acoustic impedance corresponds in the first approximation to the rigidity portion of the so-called reactance, which is in turn essentially determined by the closed air volume in the system. In measurement terms, reference is frequently made to the inverse of the reactance, the so-called compliance, the variable of which can be clearly expressed by a volume equivalent.

In the case of the auditory canal, a distinction is made between two cases.

First, in the case of a hard-walled ear-drum, no sound penetrates the inside of the ear, i.e. the compliance results almost exclusively from the air volume enclosed in the auditory canal. If a test tone with a sufficiently low frequency is tuned to a constant level in the auditory canal by way of the hearing device, the enclosed air volume can be read off from the output voltage required therefore at the hearing device amplifier (see G. Böhme, K. Weizl-Müller: "Audiometry", Publisher Hans Huber, 1998).

Second in the normal case, part of the sound penetrates the ear. The measured compliance is in this case greater and therefore corresponds to the equivalent of a larger air volume. By comparison with the measurement in the case of a hard-walled ear-drum, part of the compliance, which results from the sound conduction into the ear, can be directly calculated.

Figure 1:
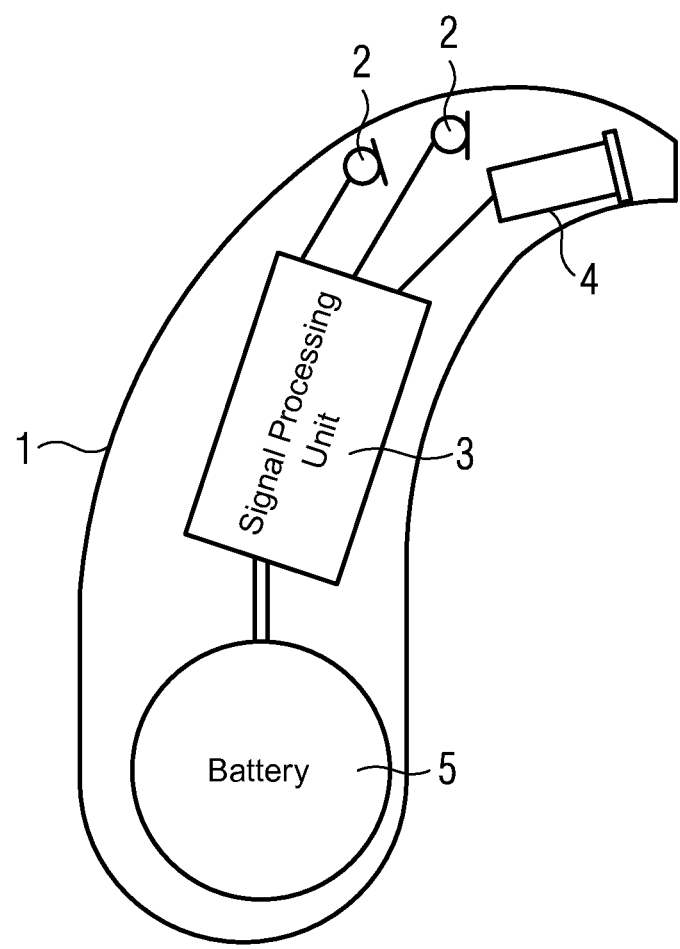
FIG. 1 is a schematic representation of a structure of a hearing device according to the prior art.
Figure 2:
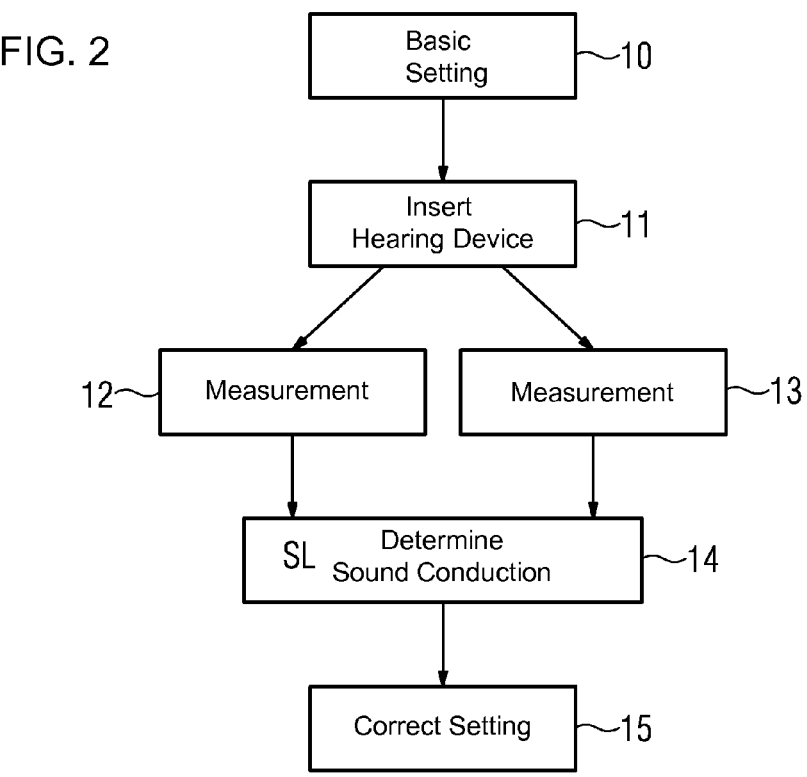
FIG. 2 is block operating diagram relating to an inventive adjustment method.
Figure 4:
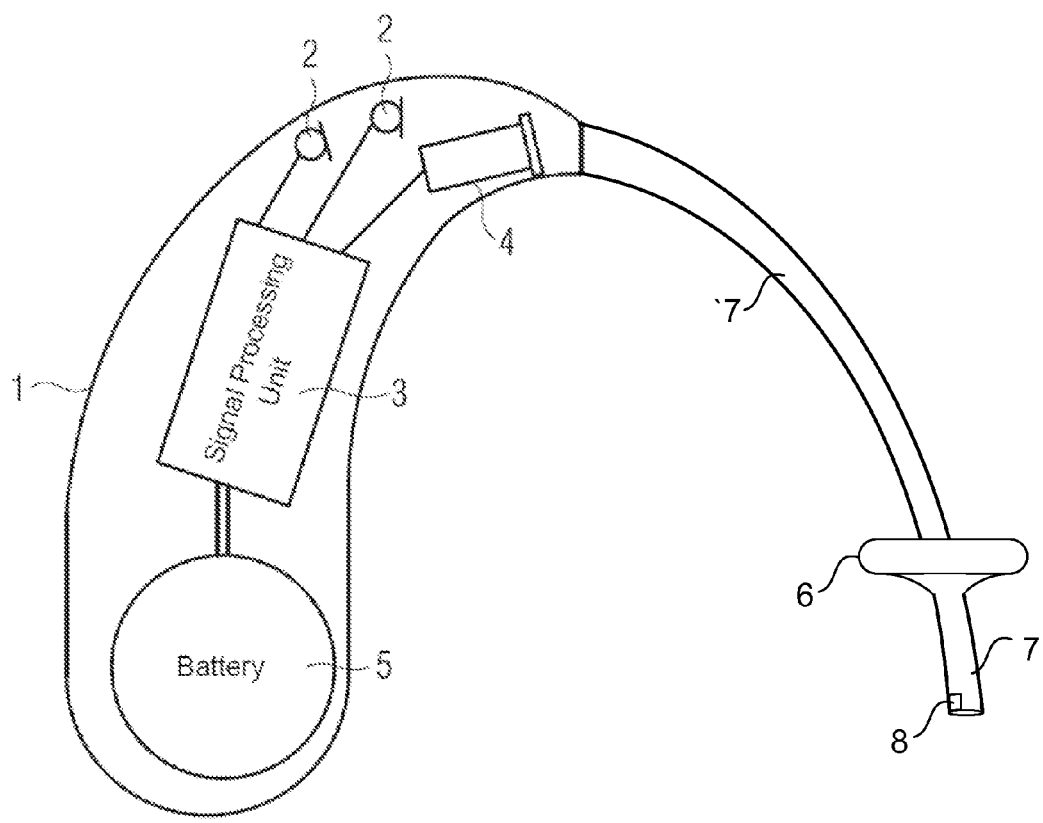
FIG. 4 is an illustration of a hearing aid with a sound tube and a microphone in the sound tube.

A typical course of action of an inventive adjustment method is explained below with the aid of FIG. 2. A hearing device is first presented with the aid of an individual audiogram for instance. The hearing device therefore obtains a basic setting, with which a hearing device wearer is able to compensate for significant parts of his/her hearing impairment. A basic setting 10 according to FIG. 2 is therefore preferably to be performed when the hearing device is not being worn. The subsequent refining of the setting takes place in-situ. To this end, the hearing device is inserted into the auditory canal in accordance with step 11. This may be an ITE hearing device for instance which is completely or almost completely inserted into the auditory canal. It may however also be a BTE hearing device, whereby only an earmold holds 6 an acoustic tube 7 in the auditory canal for instance, see FIG. 4. As described further below, the earmold must then also hold a microphone 8 or a sound output tube.

As soon as the hearing device is wholly or partially inserted into the auditory canal, two in-situ measurements 12 and 13 are implemented. The impedance and/or compliance of the acoustic system according to the hearing device, i.e. of the hearing and/or auditory system, is determined therewith. The first in-situ measurement 12 takes place when the ear-drum is in its natural state. With the second in-situ measurement 13, as described in more detail below, the ear-drum is made hard-walled so that statements relating to the auditory canal range upstream of the ear-drum can essentially be made. A sound conduction 14 from the hearing device into the ear is determined from the measurement results of the two in-situ measurements 12 and 13. With the aid of this sound conduction 14, a correction 15 of the setting of the hearing device finally takes place.

As already mentioned above, a prerequisite for the implementation of the in-situ measurements is that an additional microphone (in-situ microphone) be positioned such that sound can be received from the auditory canal. For instance, a microphone of this type can be integrated spatially closely in the hearing device together with a receiver. The additional microphone can also be an independent microphone. The in-situ microphone does not necessarily have to be located in the auditory canal, but the signals can however also be received fed in by a suitable acoustic tube. In this case, corresponding corrections are taken into consideration during the compliance calculation.

The method steps are described in more detail below from the in-situ measurements 12, 13 up to the correction 15 of the hearing device setting. Five method steps essentially result and are now described.

1. A test tone with a suitable frequency is output via the hearing device. This frequency should be sufficiently low to ensure that the measured impedance is essentially determined by the rigidity term of the reactance. On the other hand, the frequency should be too low so as to prevent low-frequency interference sound from negatively influencing the measurement. Furthermore, the selected frequency should not be whole number multiple of the usual network frequency so as to prevent the appearance of electrically induced artifacts. For these reasons conventional impedance audiometers use a frequency of 226 Hz. The test tone is set to a constant level and enables the measurement of the compliance part of the functional ear. If necessary, existing compensating bores (vent) of the hearing device are temporarily to be closed for the measurement. The sound level present in the auditory canal is registered by way of an in-situ microphone. This first in-situ measurement 12 is implemented for the ear-drum under natural conditions 2.

2. For the second in-situ measurement 13, the hearing device wearer is requested to increase the air pressure in the middle ear, by means of a so-called Valsava manoeuvre, in other words by means of an injection of air by way of the Eustachian tube, as a result of which the ear-drum is prestressed in a hard-walled fashion. Similarly to the above step 1, the compliance of the auditory canal is measured by way of the in-situ microphone, from which the enclosed air volume can be directly calculated.

3. It is possible to estimate from the volume determined in step 2 whether the auditory canal is sufficiently closed for the measurement or whether the measurement was distorted as a result of a poor fit of the device or as a result of possibly existing compensating bores. The estimation takes place by comparisons with known values of the auditory canal volume.

4. The length of the auditory canal can be estimated by means of the air volume determined in step 2 on account of knowledge of the auditory canal diameter. During in-situ audiometry, the resulting level in the plane of the ear-drum can be calculated from this length estimation by way of frequency-dependent corrections. The resulting levels result for an individual auditory canal by means of cancellations, standing waves and suchlike for instance. The auditory canal diameter for the estimation of the length of the auditory canal is known by the structure of the hearing device or of the ear mold piece.

5. The portion of sound which penetrates the middle ear can be calculated by the difference of the compliances determined in steps one and two (middle ear compliance; sound conduction 14, compare FIG. 2). Two cases are now described.

5a). The middle ear compliance is very low. This indicates a stiffening of the ossicular chain or of the ear-drum. It is possible to estimate by way of this result whether and to what extent the air conduction of the hearing device wearer is interrupted. This knowledge can be used so as to be able to estimate a sound conduction component during in-situ audiometry. In the event of an interruption in the air conduction, a wide-band additional amplification must take place for instance.

5b). The middle ear compliance is clearly increased. In this case, an interruption in the ossicular chain is probably present. Similarly to case 5a), the sound conduction is also interrupted in this case and it is possible to supplement the in-situ audiogram by means of a wide-band correction factor.

Figure 3:
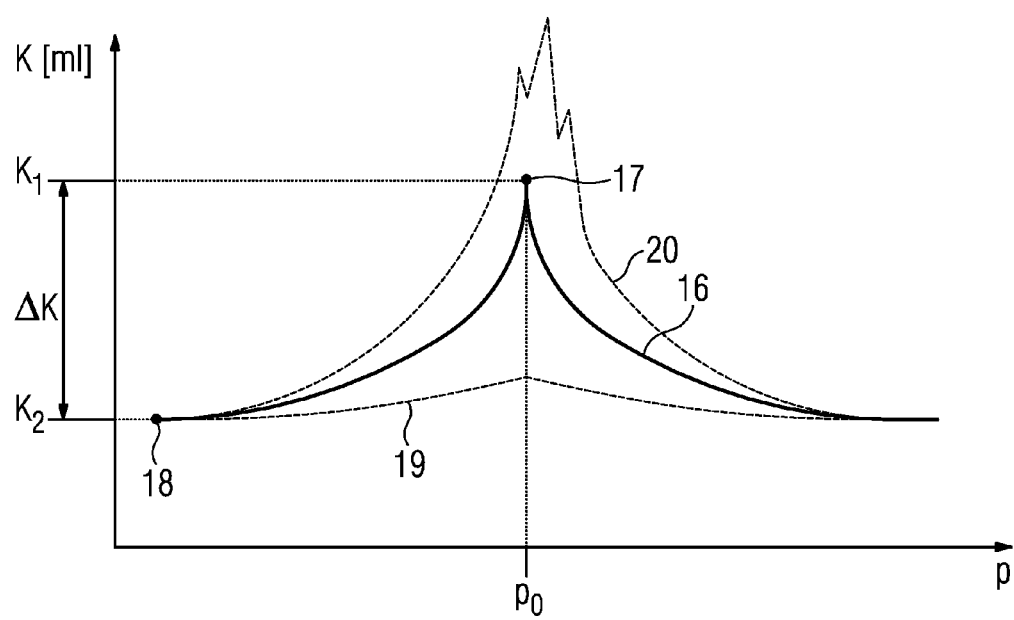
FIG. 3 is a graph showing a tympanogram.

FIG. 3 shows a tympanogram, in which the implemented in-situ measurements are reproduced in their measuring results. The continuous line 16 represents a typical tympanogram. A resonance value $K_1$ appears with a normal pressure $p_0$. This value $K_1$ can be measured by the first in-situ measurement 12 with a natural stress of the ear-drum (measuring point 17). A further measuring point 19 is determined by the second in-situ measurement 13, whereby the ear-drum is prestressed by means of the injection of air. A compliance value $K_2$ results therefrom which is smaller than the compliance value $K_1$ by the factor five to ten. The compliance $\Delta K$ determined by the air volume between the hearing device and the ear-drum is produced from the difference between the two compliance values $K_1$ and $K_2$. It represents the value for this air volume. Certain empirical values exist for this value $\Delta K$. If a measured $\Delta K$ deviates clearly from this empirical value, it is possible to assume damage of the middle ear and/or ear-drum. If the ear-drum is torn for instance, the second measuring point 18 is clearly higher and the value for $\Delta K$ is correspondingly low. A tympanogram according to curve 19 is frequently produced for older subjects. The sound conduction is hindered here as a result of less mobile ossicles in the middle ear. However, a cerumen blockage of the auditory canal may also exist. The first measuring point 17 would then be clearly lower, as a result of which a very small value $\Delta K$ likewise results.

If there is an interruption in the ossicular chain in the middle ear, a tympanogram according to curve 20 is produced in some instances. The measuring point 17 is then usually clearly higher and the compliance value $\Delta K$ is essentially above the empirical value. A correction of the signal processing of the hearing device can then be automatically implemented with the aid of the determined values $\Delta K$. An additional wide-band amplification or also only an additional amplification can be applied for instance in certain frequency ranges. Similarly, the amplification can be reduced in certain frequency ranges, in which no frequencies can be transferred on account of middle ear damage. As a result, the service life of the hearing device battery can be extended.

The inventive method for adjusting a hearing device is preferably used in the run up to an in-situ measurement and contains several advantages. An individual auditory canal correction can namely be calculated, which improves the quality of the in-situ audiogram. Additionally, this correction can be used during the calculation of the target amplification of the device and thus enables an optimum adjustment of the hearing device. Furthermore, the method enables an estimation of the sound conduction component of the in-situ audiogram and thus an improved calculation of the target amplification of the hearing device. The correct fit of the hearing device can also be examined with the aid of the inventive method. This examination can also be repeated in everyday situations, e.g. after inserting the device.

The invention claimed is:

1. A method for adjusting a hearing device to a user, which comprise the steps of:
   setting the hearing device individually to the user;
   inserting the hearing device at least partially into an auditory canal of the user;

measuring an acoustic impedance of an auditory system of the user including at least part of the auditory canal of the user in-situ;

performing the measuring being an in-situ measurement using a tympanometric method;

rendering an ear-drum for the in-situ measurement temporarily hard-walled by applying air pressure to an area of a middle ear; and automatically correcting an individual setting of the hearing device on a basis of a result of the in-situ measurement by using a difference between two in-situ measurements, one with a hard-walled ear-drum and another with a non-hard-walled ear-drum, to automatically correct the setting.

2. The method according to claim 1, wherein the individual setting of the hearing device takes place with an audiogram.

3. The method according to claim 1, wherein the hearing device contains a vent, which is temporarily closed for the in-situ measurement.

4. The method according to claim 1, which further comprises outputting a test tone with a constant level by the hearing device with a frequency between 200 Hz and 300 Hz during the in-situ measurement.

5. The method according to claim 1, wherein the in-situ measurement determines if the auditory canal is closed to a predetermined degree.

6. The method according to claim 1, which further comprises:

estimating an air volume and therefrom a distance between the hearing device and the ear-drum from the in-situ measurement; and determining a sound level of a test tone output by the hearing device being determined at the ear-drum with an aid of the distance for a correction of the individual setting of the hearing device.

7. The method according to claim 1, which further comprises increasing the air pressure to the middle ear via an Eustachian tube of a wearer.

8. A hearing device, comprising:

a signal processing facility being individually set to a user;

a section for inserting in an auditory canal of the user; and a measuring facility, with which an acoustic impedance of an auditory system of the user of exclusively at least one part of the auditory canal of the user can be measured in-situ when said section is inserted into the auditory canal, with an individual setting of said signal processing facility being automatically correctable with the aid of a tympanometric measurement, said measuring facility measuring the acoustic impedance with a tympanometric method, and a difference of two in-situ measurements, one with a hard-walled ear-drum by applying air pressure to an area of a middle ear and another with a non-hard-walled ear-drum, being used for an automatic correction of the individual setting.

9. The hearing device according to claim 8, wherein said measuring facility includes a microphone, which is integrated into said section of the hearing device which can be inserted into the auditory canal.

* * * * *